(12) United States Patent
Baecker et al.

(10) Patent No.: US 9,096,367 B2
(45) Date of Patent: Aug. 4, 2015

(54) PRODUCT HAVING BIORESORBABLE CARRIER MATERIALS AND PACKAGING

(75) Inventors: Iwer Baecker, Düsseldorf (DE); Arne Braun, Leverkusen (DE); D. I. Walther Glaubitt, Würzburg (DE)

(73) Assignee: JIANGSU SYNECOUN MEDICAL TECHNOLOGY CO., LTD., Taizhou, Jiangsu Province (CN)

(*) Notice: Subject to any disclaimer, the term of this patent is extended or adjusted under 35 U.S.C. 154(b) by 507 days.

(21) Appl. No.: 13/320,181

(22) PCT Filed: May 21, 2010

(86) PCT No.: PCT/EP2010/003146
§ 371 (c)(1),
(2), (4) Date: Jan. 30, 2012

(87) PCT Pub. No.: WO2010/139407
PCT Pub. Date: Dec. 9, 2010

(65) Prior Publication Data
US 2012/0125798 A1 May 24, 2012

(30) Foreign Application Priority Data
May 30, 2009 (EP) .................................. 09007271

(51) Int. Cl.
*B65D 81/26* (2006.01)
*B65D 1/04* (2006.01)
*A61F 15/00* (2006.01)
(Continued)

(52) U.S. Cl.
CPC ............ *B65D 81/261* (2013.01); *A61F 15/001* (2013.01); *B65D 77/003* (2013.01); *B65D 81/266* (2013.01); *A61B 2017/00004* (2013.01); *A61B 2019/0273* (2013.01); *A61B 2019/0278* (2013.01); *A61F 2013/00221* (2013.01)

(58) Field of Classification Search
CPC .. B65D 81/261; B65D 81/266; B65D 77/003; A61F 15/001
USPC ......... 206/204, 205, 210, 363, 438, 570–572; 53/467, 473
See application file for complete search history.

(56) References Cited

U.S. PATENT DOCUMENTS 4,730,726 A * 3/1988 Holzwarth .................... 206/204
5,322,161 A * 6/1994 Shichman et al. ............ 206/204
(Continued)

FOREIGN PATENT DOCUMENTS

DE  102004063599   7/2006
EP  1262542         12/2002
(Continued)

OTHER PUBLICATIONS

L.D. Hinkle "Effect of purge pressure on desorbing water removal rate", Journal of Vacuum Science and Technology A: Vacuum, Surfaces and Films, Jul./Aug. 2004, vol. 22, No. 4, pp. 1799-1803.
(Continued)

Primary Examiner — Luan K Bui
(74) Attorney, Agent, or Firm — Miles & Stockbridge PC (57) ABSTRACT

The present invention relates to a product containing bioabsorbable carrier materials especially for tissue regeneration and to a packaging, and also to processes for the production of the product.

8 Claims, 3 Drawing Sheets

(51) Int. Cl.
  *B65D 77/00* (2006.01)
  *A61B 17/00* (2006.01)
  *A61B 19/02* (2006.01)
  *A61F 13/00* (2006.01)

(56) References Cited

U.S. PATENT DOCUMENTS

| | | | |
|---|---|---|---|
| 5,375,698 A * | 12/1994 | Ewart et al. | 206/205 |
| 6,269,946 B1 | 8/2001 | Colombo | |
| 6,530,472 B2 * | 3/2003 | Hacikyan | 206/204 |
| 6,907,992 B2 * | 6/2005 | McMichael et al. | 206/571 |
| 7,960,602 B2 | 6/2011 | Thierauf et al. | |
| 2004/0004019 A1 * | 1/2004 | Busch | 206/571 |
| 2007/0144922 A1 * | 6/2007 | Imoarai et al. | 206/204 |
| 2009/0099579 A1 | 4/2009 | Nentwick et al. | |
| 2009/0194451 A1 * | 8/2009 | Leiner et al. | 206/524.1 |
| 2010/0274205 A1 * | 10/2010 | Morelli et al. | 206/570 |
| 2011/0183419 A1 | 7/2011 | Glaubitt | |

FOREIGN PATENT DOCUMENTS

| | | |
|---|---|---|
| FR | 2660634 | 10/1991 |
| GB | 2103565 | 2/1983 |
| JP | 2006068085 A | 3/2006 |
| JP | 2009095667 A | 5/2009 |
| WO | 0142428 | 6/2001 |
| WO | 2008086970 | 7/2008 |

OTHER PUBLICATIONS

Gorbach et al., "Measurement and Modeling of Water Vapor Adsorption on Zeolite 4A-Equilibria and Kinetic", Adsorption, 2004, vol. 10, No. 1, pp. 29-46.
Grubner et al., "Molekularsiebe", Molecular Sieve, Berlin, Duetscher Verlag der Wissenschaften 1968, pp. 88-89.
Cekova et al., "Zeolites as alcohol adsorbents from aqueous solutions", Acta Periodica Technologica, 2006, Issue 37, pp. 83-87.
International Search Report mailed Aug. 8, 2010; International Application No. PCT/EP2010/003146; Filed May 21, 2010.

* cited by examiner

PRODUCT HAVING BIORESORBABLE CARRIER MATERIALS AND PACKAGING

CROSS REFERENCE TO RELATED APPLICATIONS

This application is a §371 National Stage Application of PCT/EP2010/003146, filed May 21, 2010, which claims priority to EP0900727.1, filed May 30, 2009.

BACKGROUND OF THE INVENTION

1. Field of the Invention

The present invention relates to a product containing bioabsorbable carrier materials, in particular for tissue regeneration, and a packaging, and also to processes for the production of the product.

2. Description of Related Art

It has been found with bioabsorbable carrier materials for tissue regeneration, such as, for example, wound dressings of silica gel fibers or webs, that over storage periods in the region of several months or years the biodegradation properties of the carrier materials are adversely affected. It has been shown, in particular, that bioabsorbable carrier materials that were stored in conventional packagings have a delayed bioabsorbability or incomplete bioabsorbability. The latter can lead to residues remaining in the tissue, which over a longer time can cause inflammatory reactions and lead to non-physiological wound healing. The subject of the present invention is that it has now surprisingly been found that the biodegradation properties of the bioabsorbable carrier materials can be guaranteed over a long period of time by suitable packaging materials. This is of particular importance especially in connection with the storage of bioabsorbable carrier materials for tissue regeneration, such as, for example, bioabsorbable wound dressings of silica gel.

Wound dressings of bioabsorbable carrier material are proposed for the treatment of poorly healing wounds, as are present, for example, in the case of diabetes-related ulcers, decubitus, burn injuries or alternatively surgical wounds. Here, the absorption behavior of the material during the healing process is of central importance for the success of treatment. Wound dressings based on silica gel are excellently suitable, inter alia, on account of their bioabsorption properties and their biocompatibility for use in the healing of poorly healing wounds. Depending on the application type and nature of the wound, a specific absorption behavior is needed, which must be maintained over the storage period of the product. In addition to the maintenance of the biodegradation properties, the guarantee of stability by mechanical protection of the wound dressings during storage and transport is a further important aspect that must be heeded in the provision of a suitable packaging. External influences, such as occur, for example, during transport, can initiate movements of the wound dressing relative to the packaging, which cause fraying of the corners and edges and lead to fiber detachment or fiber fracture, which is undesirable during application for esthetic and practical reasons. Therefore a form is needed that restricts the relative movements in all directions to a minimum. Here, on account of the compressibility of the material—especially in the case of larger dimensions of the wound dressing in the region of 10 cm×10 cm or more—to keep as low as possible or to avoid mechanical fixing, which causes surface pressure on the material, as could be achieved, for example, by vacuum in a flexible system. Furthermore, in the case of simple packaging in a laminated film pouch inadequate protection against mechanical action from outside is afforded, which can lead to damage to the wound dressing. No products are described in the prior art that can guarantee the biodegradation properties and the stability against mechanical action and slipping of bioabsorbable carrier materials for tissue regeneration. There is therefore a need for products containing bioabsorbable carrier materials, in particular for tissue regeneration, that can prevent the loss of the bioabsorption properties of the bioabsorbable carrier materials. At the same time, the products must protect the bioabsorbable carrier materials adequately against mechanical action.

SUMMARY

The object of the present invention was accordingly to provide products containing bioabsorbable carrier materials, especially for tissue regeneration, which address the existing disadvantages and fulfil the abovementioned requirements with respect to guaranteeing the biodegradation properties and the mechanical protection. According to the invention, the object is achieved by the provision of a product comprising:

a) a packaging of
  1) a mechanically stable base element (1) having at least one cavity (2a) open towards at least one side, for the removal at least of one bioabsorbable carrier material arranged in the cavity (2a),
  2) at least one adsorbent,
  3) at least one sealing foil (3) that closes at least the opening of the cavity, which contains a bioabsorbable carrier material embedded therein, and
  4) optionally a pouch (4) made of aluminium foil or laminated aluminium foil, which completely surrounds and closes the base element (1) with sealing foil (3), and/or a mechanically stable base element (1) optionally additionally comprising a metal foil of aluminium foil or laminated aluminium foil, b) a bioabsorbable carrier material, which is situated at least in one cavity (2a) of the mechanically stable base element (1) of the packaging.

The product according to the invention is surprisingly distinguished by guaranteeing the biodegradation properties of the bioabsorbable carrier materials, stability against external mechanical actions and/or movements, and simple handling during application.

Within the meaning of the present invention, the expression "bioabsorbable" or "biodegradable" designates the property of the carrier material of being degraded if the carrier material is exposed to conditions that are typical of those that are present in a tissue regeneration (for example of a wound or cartilage or bone medium). The bioabsorbable or biodegradable carrier materials are "bioabsorbable" or "biodegradable" within the meaning of the invention especially if they completely dissolve after 48 hours, preferably 36 hours and particularly preferably after 24 hours, in a 0.05 M tris pH 7.4 buffer solution (Fluka 93371) thermostatted at 37° C. (see Example 3).

Suitable bioabsorbable carrier materials (without being restricted thereto) are, for example, silica gel, polyglycolic acid, polylactic acid, polydioxanone, polylactide co-glycolide, poly-ε-caprolactone, polyanhydride, polyphosphazene, polyorthoester, alginate, chondroitin-6-sulphate, chitosan, hyaluronic acid, collagen, polylysine, dextran, heparin etc. Preferred bioabsorbable carrier materials according to the invention are those that can be employed for tissue regeneration. The expression "carrier materials for tissue regeneration" is understood as meaning surface elements and/or three-dimensional spatial elements that consist of a bioabsorbable material and assist tissue regeneration. The bioabsorbable material can be employed for the regeneration of any desired tissue such as, for example, epithelia, endothelium, urothelium, mucosa, dura, connective tissue etc. Thus it is possible, for example, to employ a surface element (wound dressing) as a bioabsorbable carrier material for wound healing. For cartilage or bone regeneration a surface element and/or a three-dimensional spatial elements is used. Preferred bioabsorbable carrier materials are those that are based on silica gel. Silica gel carrier materials can comprise silica gel fibers, webs, monoliths, hydrogels and/or powders. Preferred bioabsorbable carrier materials are those that are based on silica gel fibers and/or silica gel webs. Wound dressings based on silica gel fibers and/or silica gel webs as are described, for example, in DE 102004063599B4 or WO2008086970A1 are particularly preferred. Further bioabsorbable carrier materials based on silica gel are skin implants such as are known from WO200142428A1 or cell combinations, lead structures, tissue or composite grafts such as are described in EP1262542A2. The present invention, however, is not restricted only to products containing bioabsorbable carrier materials for tissue regeneration especially based on silica gel. The products according to the invention can also comprise materials based on silica gel, which relate to other applications (as carrier materials for tissue regeneration).

The mechanically stable base element (1) according to the invention consists of customary plastics such as, for example, polyethylene terephthalate glycol (PETG), polyvinyl chloride (PVC), COC (cycloolefin copolymer, e.g. Topas®, cycloolefin polymer (COP), polychlorotrifluoroethylene (e.g. ACLAR®), polyethylene (PE), polypropylene, polyvinylidene chloride (PVDC), polycarbonate, polyester, polyacrylate, polyamide or other plastics.

The mechanically stable base element can optionally contain a metal foil of aluminium foil or a laminated aluminium foil. In this embodiment of the invention, for example, a deep drawn aluminium dish containing a laminated aluminium foil is optionally sealed under slight vacuum with a laminated aluminium foil. The aluminium dish is internally provided (i.e. on the side where the bioabsorbable carrier material or the adsorbent is received) with a sealing wax and/or a polymer-based coating. On the outside, the aluminium dish can optionally be reinforced by a plastic blister. The sealing foil (3) in this embodiment of the invention is also preferably an aluminium foil or a laminated aluminium foil.

The mechanical stability of a base element is guaranteed if the flexural stiffness and the stability to buckling is so high that on withdrawing the sealed-on foil the shape of the base element is to the greatest possible extent retained, so that the user can safely remove the bioabsorbable carrier material and especially a wound dressing and, for example, falling out is excluded in the case of proficient handling. The stiffness can be guaranteed by, for example, choice of the material strengths and also by profiling of the base element (1) during deep-drawing. The base element is a surface in which at least one cavity is formed. In a preferred embodiment of the invention, the mechanically stable base element (1) comprises a second cavity (2b) for receiving an adsorbent. In the presence of a second cavity, the sealing foil (3) preferably closes the openings of both cavities (2a and 2b).

The surfaces of the base element, seen from the cavities, are preferably plane. The openings of the cavities are preferably on the same side of the base element. A planar base element can take any desired geometric shape. Preferably, the base element is quadrangular. The base element can also take on the function of a sterile barrier. In the preferred embodiment of the invention, the at least two cavities of the base element are arranged in a row, in parallel, circularly, spirally or in a number of rows and can take any desired geometrical shape, such as, for example, round, rectangular, hexagonal etc. Preferably, the cavity for receiving the bioabsorbable carrier material is quadrangular and here especially the wound dressing is quadrangular. In a preferred embodiment, the cavity (2a) for the receiving the wound dressing contains a further recess (11), which facilitates the removal of the wound dressing, but does not influence the mechanical fixing of the wound dressing in the cavity (2b). The recess (11) in this embodiment of the invention is designed such that it only takes up a section of a cavity wall (10).

The cavity (2b) for receiving the adsorbent can be open or closed. In the latter case, the base element is shaped during production so that it itself forms a closed void with an adsorbent material contained therein. Between the cavity (2a) and the cavity (2b) a bridge (9) is present, which is formed by the base element. The bridge can also only be designed in some cases so that, for example, the sealing foil (3) on closure of the cavities (2a) and (2b) does not come into contact with the bridge (9).

Surprisingly, it has been found that by the addition of a least one adsorbent to the packaging according to the invention the biodegradability of the carrier material can be guaranteed over a long period of time. In the case of carrier materials based on silica gel, the at least one adsorbent is an adsorbent for water and/or ethanol.

Preferably, one or more adsorbents for water and for ethanol are employed. Adsorbents for water and/or ethanol are known from the literature. Suitable adsorbents for water, for example, are silica gels and/or zeolites having a pore diameter in the range from 2-5 nm (Hinkle, L. D., "Effect of purge pressure on desorbing water removal rate" Journal of Vacuum Science and Technology A: Vacuum, Surfaces and Films 2004, 22 (4), 1799-1803/Gorbach, A.; Stegmaier, M.; Eigenberger, G., "Measurement and Modeling of Water Vapor Adsorption on Zeolite 4A-Equilibria and Kinetic." Adsorption 2004, 10 (1), 29-46/Grubner, O. et al., "Molekularsiebe" [Molecular sieve], Berlin, Deutscher Verlag der Wissenschaften 1968). Silica gel, zeolite 3A and zeolite 4A may be mentioned by way of example.

Suitable adsorbents for ethanol are, for example, Silicalite-1, F-Silicalite and ZSM-5 (Cekova Blagica et al., "Zeolites as alcohol adsorbents from aqueous solutions", Acta periodica technologica, iss. 37, pp. 83-87, 2006).

By means of silica gel as an adsorbent in the packaging according to the invention, a biodegradability of a carrier material based on silica gel can be achieved for a storage time of several weeks (see Example 3). Silica gel is suitable here as an adsorbent for water and ethanol. Ethanol and water differ, inter alia, in their molecular size. An adsorbent especially suitable for ethanol therefore has a pore diameter adapted to the molecular size of ethanol, while an adsorbent especially suitable for water has a diameter adapted to the molecular size of water.

Surprisingly, it has been shown that by addition of two different adsorbents to the packaging according to the invention, of which one is especially suitable for water and the other is especially suitable for ethanol, a product is obtained in which a biodegradability of over several months is guaranteed (see Example 3).

Preferably, the product according to the invention therefore comprises at least two adsorbents, where at least one of the adsorbents is an adsorbent for water (such as, for example, zeolite 3A or zeolite 4A) and at least one of the adsorbents is an adsorbent for ethanol (such as, for example, Silicalite-1).

One or more adsorbents can here be incorporated within (i.e., for example, in the cavity provided for this or in another position within the base element) and/or outside (i.e. in the pouch, but not in the cavity provided for this) of the base element. Preferably, the adsorbent is/the adsorbents are incorporated into the cavity of the base element provided for this. Handling is simplified by means of this, as the adsorbent cannot fall out of the pouch. One or more adsorbents can be added in other embodiments, however, for example also as a monolith in the cavity (2a) and are covered by a permeable film. The bioabsorbable carrier material (for example a wound dressing) is then added to this film. Alternatively, one or more adsorbents can also be introduced into a small pouch and sealed in this form under the laminated aluminium foil to be sealed, i.e. the sealing foil (3).

The quantitative ratio between the bioabsorbable carrier material based on silica gel and the adsorbent material is preferably between 2:1 and 1:20 and particularly preferably between 1:2 and 1:10.

Figure 1:
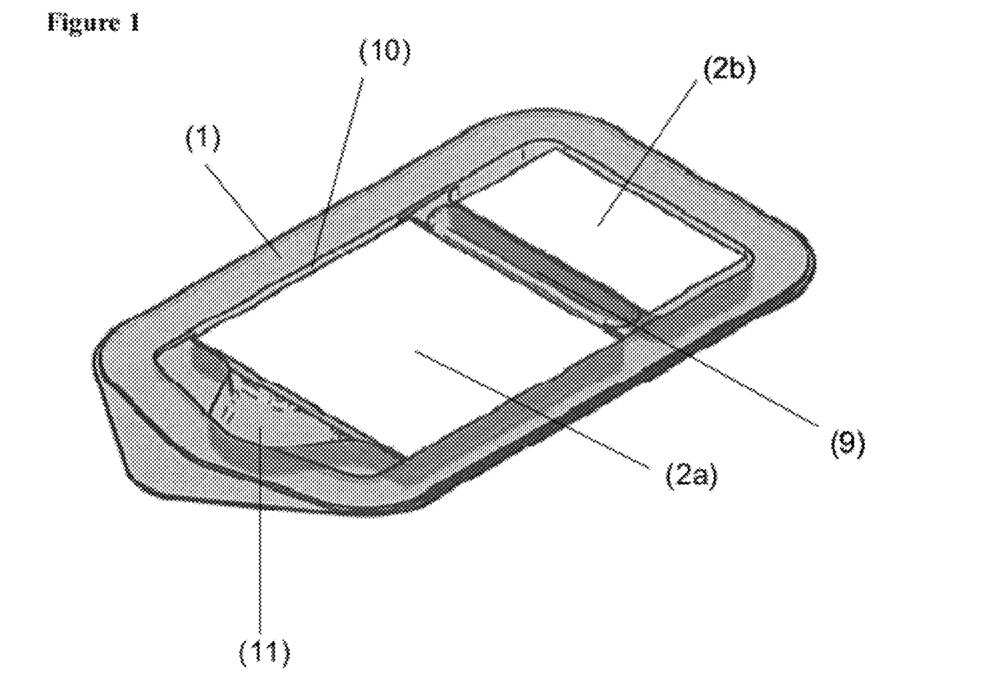
FIG. 1 shows an example of a base element with cavities from below.
Figure 2:
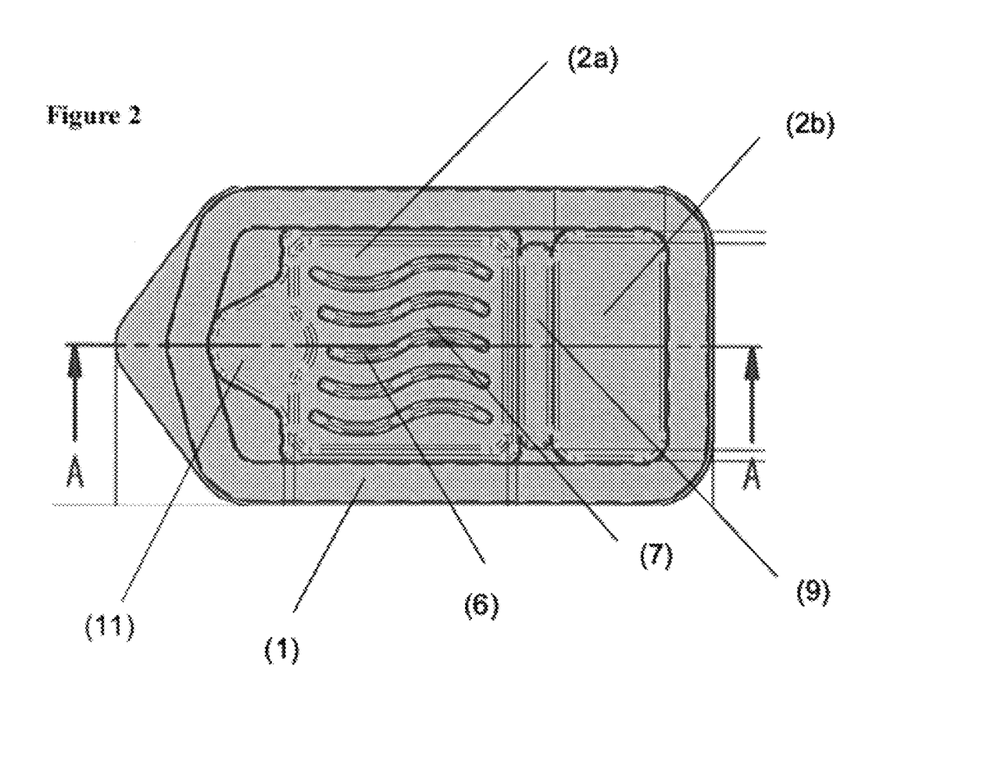
FIG. 2 shows an example of a base element with cavities represented in plane view.
Figure 3A:
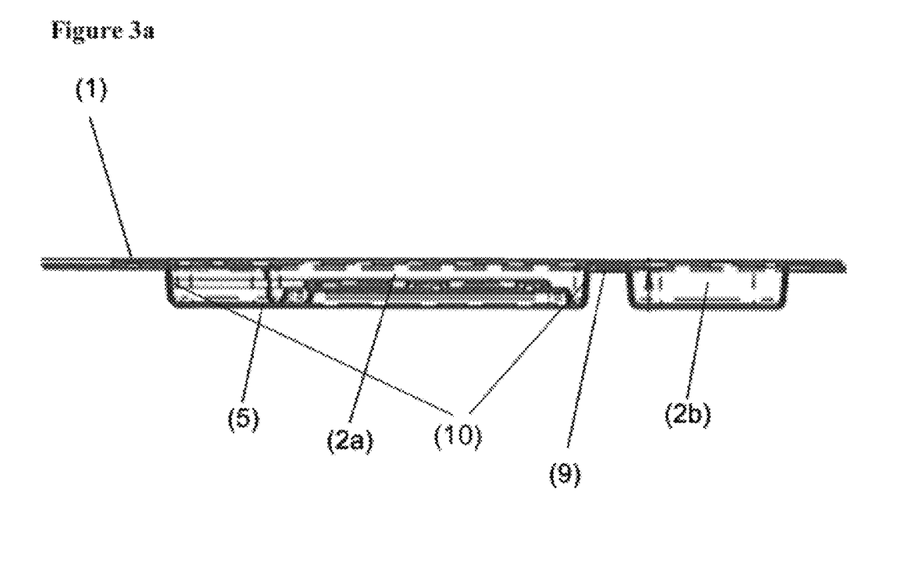
FIG. 3a shows an example of a base element with cavities from the side.
Figure 3B:
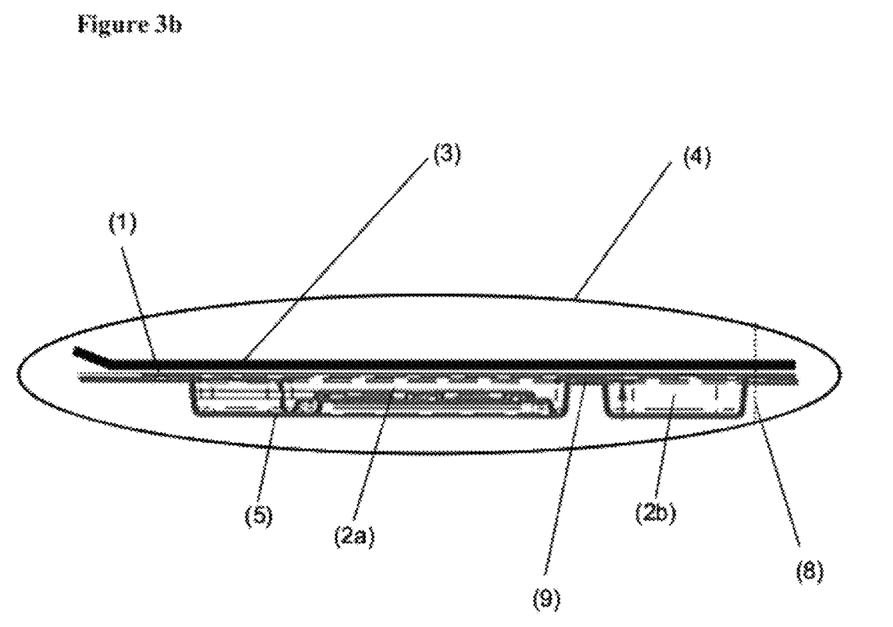
FIG. 3b shows an example of a base element with cavities, the sealing foil (3) and the optionally present pouch (4) from the side.
Figure 4A:
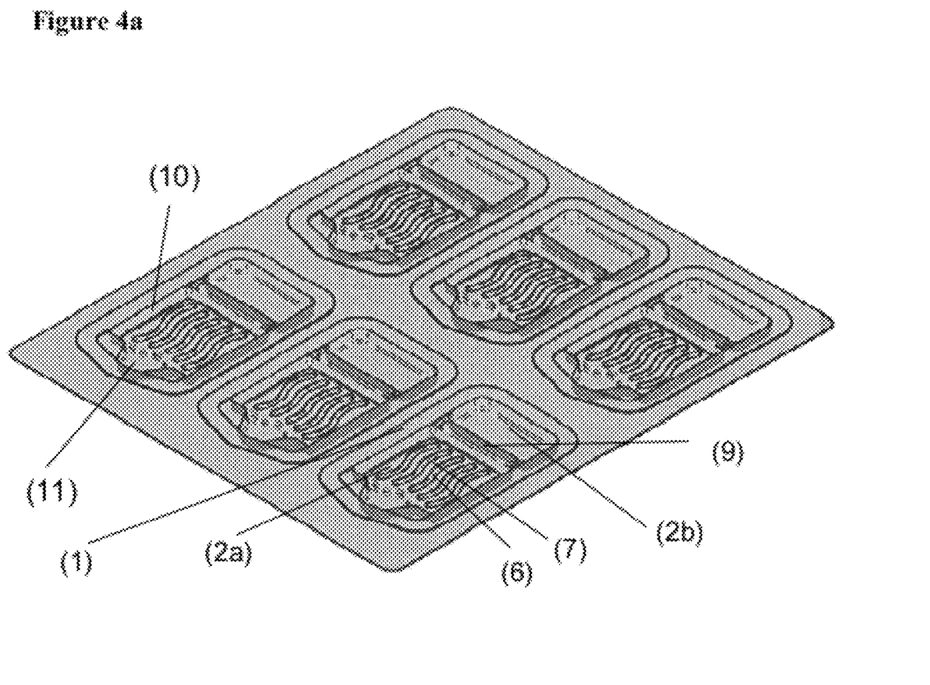
FIG. 4a shows an example of a base element with a number of cavities (2a and 2b).
Figure 4B:
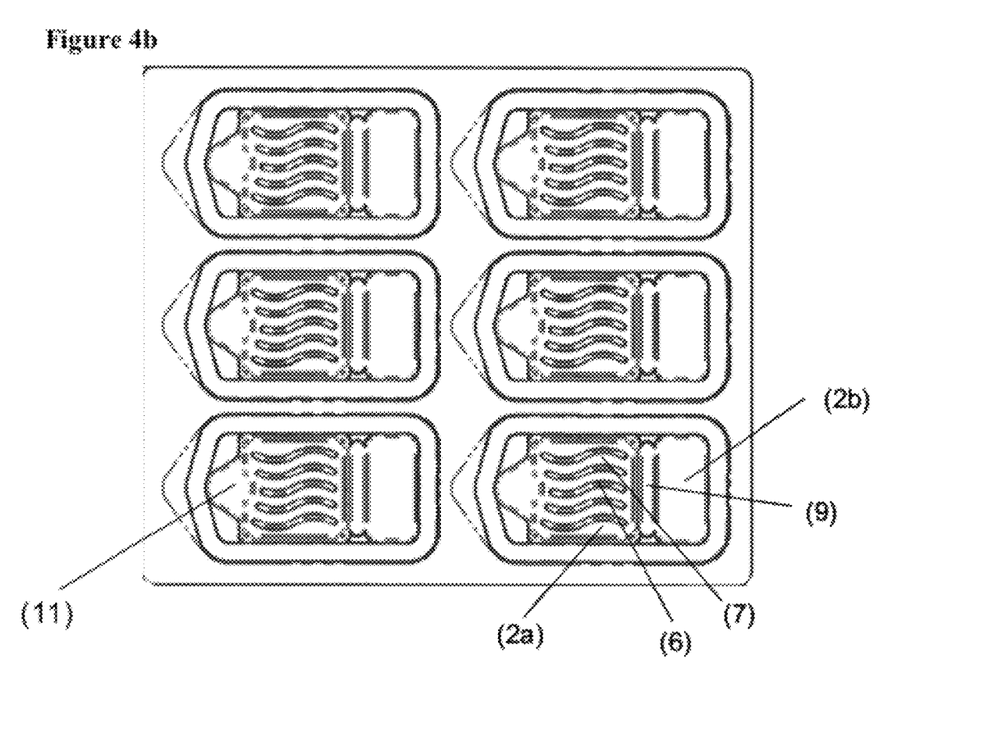
FIG. 4b shows an example of a base element with a number of cavities (2a and 2b) represented in plane view.

According to the invention, at least the opening of the cavity of the base element, which contains an absorbable carrier material embedded therein, is closed by a sealing foil (3) (by heat sealing the foil to the base element). The sealing foil prevents the penetration of particles and makes possible, for example, removal of the bioabsorbable carrier materials in the presence of a pouch (4), without said materials being able to fall out already on opening the pouch (4). The sealing foil is a metal foil and/or polymer film. The sealing foil, however, can also itself be a pouch of aluminium foil or laminated aluminium foil. In this case, the sealing foil, for example, can close the openings of the base element such that the base element, the adsorbent and the bioabsorbable carrier material are completely surrounded by the sealing foil (as a pouch). In this embodiment, the sealing foil does not have to be bonded to the base element, for example by heat-sealing, but can be closed with itself, (i.e. sealed), e.g. under slight vacuum. The sealing foil (3) can be made from the same materials as the base element. For example an aluminium foil or laminated aluminium foil is used as the metal foil. A film based on Tyvek (DuPont), for example, can be used as the polymer film. The aluminium layer of the aluminium foil or laminated aluminium foils of the present invention preferably has a layer thickness of at least 10 μm, particularly preferably at least 16 μm. The aluminium foil or laminated aluminium foil consists in a preferred embodiment of the invention of a number of layers. For example, the foil is three-layered and consists from outside to inside of PET, aluminium and PE. In a further preferred embodiment of the invention, an additional pouch of aluminium foil or laminated aluminium foil (4) surrounds the base element (1) with sealing foil (3) and the adsorbent and the bioabsorbable carrier material situated in the cavity of the base element completely and closes this (e.g. by heat sealing with itself). In a particularly preferred embodiment of the invention, the pouch consists of at least two different layers, in which the bonding between the inner layer (i.e. the layer that comes into contact with the base element and the sealing foil) and the aluminium foil takes place by heat lamination. The use of an adhesive can be dispensed with here. Alternatively, glues or adhesives are preferred, in the preparation of which no isocyanates have been employed. Traces of, for example, methylene diisocyanate (MDI) or toluene diisocyanate (TDI) can cause undesirable discolorations in conjunction with secondary components in the silica gel fibers. Laminated films of the design described are obtainable on the market, for example from Amcor. The pouch is closed so that the base element with sealing foil is situated in the pouch. In a preferred embodiment, the film pouch or a part thereof is peelable for easy opening by the user or equipped with a zipper (shown in FIG. 3b by (8)).

A preferred embodiment of the present invention relates to a product comprising a packaging, in which the cavity (2a) of the mechanically stable base element (1) is equipped for the removal at least of one wound dressing arranged in the cavity (2a), which is designed in height, breadth and length so that slipping of the wound dressing in the cavity in one of the three dimensions is essentially made impossible. The basic principle here is that as a result of narrow gap widths between the edge of the cavity and wound dressing the relative velocity between wound dressing and blister in the case of external mechanical action (e.g. vibration) is closely restricted, so that in the case of impacts of the wound dressing against the blister the transmitted energy is so low that even on repeated stress no product damage occurs. Accordingly, for the mechanical protection of the wound dressing the dimension of the cavity of the base element for receiving the wound dressing is matched closely to the dimensions of the wound dressing. A side edge distance of the wound dressing to in each case one of the cavity walls (10) of less than approximately 1 mm, very particularly preferably of less than approximately 0.5 mm, is particularly preferred. By means of this, lateral slipping is prevented, which can lead to fraying, especially in the corners. The height of the cavity (from the floor plate (5), or from one bridge (7) to the sealing foil) for receiving the wound dressing exceeds the thickness of the wound dressing by less than approximately 5 mm, particularly preferably by less than approximately 2 mm. By this means, the wound dressing is mechanically fixed in the cavity in all 3 dimensions (height, breadth, length). The wound dressing preferably has the following dimensions: 2.5×2.5 cm to 20×20 cm. The following is accordingly illustrative—with a 10×10 cm wound dressing the cavity for receiving the wound dressing is shaped in the following way: length and breadth of the cavity preferably in each case approximately 10.01-10.1 cm; height corresponds to the thickness of the wound dressing plus additionally preferably 0.3 mm to 5 mm.

The risk of fraying of the wound dressing can be further reduced by punching out the wound dressing from the web fabric, so that round or angular shaped parts result. In the case of angular shaped parts such as, for example, a square or hexagon, the punching tools are constructed so that the corners of the wound dressing are rounded off.

In a further preferred embodiment, the product according to the invention comprising a packaging is shaped such that the cavity (2a) of the mechanically stable base element (1) has, for the removal at least of one wound dressing arranged in the cavity (2a), a floor plate (5) with channels (6) for receiving wetting fluid and bridges (7) for the drainage of the wetting fluid during removal. As a result of the design of the floor plate with channels and bridges, a hydrophobic wound dressing can be wetted with an (isotonic) salt solution or buffer solution before removal (e.g. with forceps). By means of this a simplified (complication-free) application of the wound dressing directly to the skin is made possible and a more rapid and extensive exchange with the wound tissue and wound exudate is guaranteed. The distance between bridges, i.e. the channel width is at least so large that its wetting takes place with the wetting fluid and this can simply drain away. The channel width here is to be chosen to be so small that the wetted wound dressing for the purpose of handleability does not sag between bridges. The width of the bridges is preferably chosen so that adequate support of the wound dressing is guaranteed. Further aspects in the choice of the number and dimensions of the bridges or channels are the deep-drawability of the respective material and esthetic points of view.

A further preferred embodiment relates to the product according to the invention comprising a packaging in which the cavity (2b) of the mechanically stable base element (1) is open for receiving an adsorbent on at least one side of the base element and the sealing foil closes the openings of the least two cavities (2a and 2b) of the base element which are open towards at least one side with formation of cavities and the sealing foil can be peeled off by a user only for the removal at least of one bioabsorbable carrier material arranged in the cavity (2a). In the case of the integration of the adsorbent in a cavity (2b) of the base element, contact with a wetting fluid should be avoided. For this, this (second) cavity (2b) should be closed with a sealing foil and also not be opened on opening the cavity (2a), which contains the bioabsorbable carrier material for tissue regeneration.

In a further preferred embodiment according to the invention, a recess is therefore located on the bridge (9) between the sealing foil, which closes the cavity with the bioabsorbable carrier material (2a) that closes the cavity with the adsorbent (2b). Alternatively, by perforation of the sealing foil sealed to the bridge (9), a defined tear-off edge can be created. Thus the cavity of the base element receiving the adsorbent remains closed on opening the sealing foil.

In an alternative embodiment of the invention, the adsorbent material is integrated into the cavity of the base element in such a way that it is completely surrounded by the base element and no longer has to be closed by a sealing foil. The cavity for receiving the adsorbent in this embodiment of the invention forms a closed-off void formed by the base element itself.

The present invention furthermore also relates to a process for the production of a product according to the invention in which a) in a packaging with a mechanically stable base element (1) with at least one cavity (2a) open towards at least one side, at least one bioabsorbable carrier material is inserted into the cavity (2a) for the removal at least of one bioabsorbable carrier material in the cavity (2a), b) a sealing foil (3) at least the cavity, which contains a bioabsorbable carrier material embedded therein, is closed such that either a heat-sealed bond completely surrounding the cavity results between the sealing foil (3) and a part of the base element (1) or a heat-sealed bond results between parts of the sealing foil (3) itself, so that the base element and the bioabsorbable carrier material are situated in the sealing foil (3) after closure, c) optionally the mechanically stable base element is sealed with the cavity closed by the sealing foil (3) with a pouch (4) of aluminium foil or laminated aluminium foil, which completely surrounds the base element (1) with sealing foil (3), and/or the mechanically stable base element (1) is optionally additionally equipped with a metal foil of aluminium foil or laminated aluminium foil, and d) at least one adsorbent, in the case of silica gel as a carrier material preferably an adsorbent for water and an adsorbent for ethanol, is added to the packaging before the sealing in step b) or c).

If in the case of a mechanically stable base element (1) a second cavity (2b) is present, the sealing foil (3) preferably closes both cavities. The at least one adsorbent is then inserted into the cavity (2b) before the heat sealing with the sealing foil (3). Alternatively, the at least one adsorbent can also be introduced into a small pouch and sealed under the sealing foil (3) in this form. In this embodiment, only one cavity (2a) can be present as long as sufficient space is available for the bioabsorbable carrier material and the at least one adsorbent. In this embodiment too, the at least one adsorbent must additionally be introduced into the cavity before the heat sealing. Alternatively, the adsorbent can be added to the pouch (4) of aluminium foil or laminated aluminium foil before the sealing of the pouch. In a further embodiment of the invention, the cavities of the base element are flushed with an anhydrous inert gas (such as, for example, nitrogen) before the sealing of the sealing foil (3).

If the packaging is designed such that the cavity (2b) is open for receiving an adsorbent on at least one side of the base element and the sealing foil (3) closes the openings of the at least two cavities (2a and 2b) of the base element which are open towards at least one side with formation of cavities and the sealing foil can be peeled off by a user only for the removal at least of one bioabsorbable carrier material arranged in the cavity (2a), then during production, for example, two separate sealing foils for cavity (2a) and for (2b) can be heat-sealed. In a further embodiment, also only one sealing foil (3) can be applied, which is then perforated on the bridge (9), so that a defined tear-off edge results.

As a mechanically stable base element, according to the invention either prefabricated blisters (base element with cavity(cavities)) are employed or the blisters are deep-drawn from a plastic film on a deep-drawing machine. Thereafter a bioabsorbable carrier material, preferably a wound dressing, and an adsorbent are inserted into the cavities of the base element which are provided for this. Subsequently, the sealing foil is applied and the foil is bonded to the blister by heat-sealing. The closed blister is preferably introduced into a prefabricated aluminium foil pouch or laminated aluminium foil pouch and the last seam is heat-sealed by means of a sealing machine. Alternatively, the pouch can be produced in a 4-sides sealing machine from an aluminium foil or laminated aluminium foil. The further packaging, e.g. in folding boxes, labelling, addition of package inserts etc. is carried out analogously to the known prior art.

The present invention also relates to a use of the packaging described in this application for the packaging and storage of the bioabsorbable carrier materials described in this application.

The invention is intended to be illustrated in more detail using the following figures and examples, without being restricted thereto.

FIGURES

Legend (1): Base element
(2a): Cavity (2a) for the removal at least of one bioabsorbable carrier material arranged in the cavity (2a)

(2b): Cavity (2b) for receiving an adsorbent
(3): Sealing foil
(4): Pouch
(5): Floor plate of the cavity (2a)
(6): Channel or channels for receiving wetting fluid
(7): Bridge for the drainage of the wetting fluid
(8): Zipper or element which facilitates the opening of the pouch (4)
(9): Bridge between the cavity (2a) and the cavity (2b)
(10): Cavity wall or cavity walls
(11): Recess for simplified product removal from the cavity (2a)

EXAMPLES

Example 1

Description of the Production of the Bioabsorbable Carrier Materials (Bioabsorbable Wound Dressings)

The synthesis of the bioabsorbable wound dressings used for the examples described below (hydrolysis/condensation, reactive evaporation and maturation) was carried out as described in detail in WO2008086970A1. The essential process parameters are summarized below:
Hydrolysis/Condensation:
  in a 2l stirring vessel
  in molar ratios
  reaction period about 19 h
  stirred at 150 rpm
  2 h adiabatic procedure, subsequently isothermal at 37° C.
Reactive Evaporation:
  in a 2l stirring vessel
  process: evaporation by means of overclouding of control air
  isothermal procedure at 63° C.
  reaction period about 5:20 h
  stirred at 60 rpm
  viscosity at the end (4° C.; 10 s$^{-1}$): 0.95 Pas
Maturation:
  in a 500 ml maturation beaker
  maturation temperature 4° C.
  maturation period (polymerization): 21 d
After Intermediate Storage at −80° C. Spinning Took Place:
  during spinning temperature adjustment of the sol to about −12° C.
  spinning turret feed air: temperature 25° C., dew point 0° C.
  use of a 19-nozzle hole plate
  conditioning of all webs in the isolator box for about 40 min
  cut of the web (5 cm×5 cm) Web corresponds to the bioabsorbable wound dressing discussed in this application Example 2

Packaging of the Bioabsorbable Wound Dressings

The wound dressing was laid in a blister according to the invention. One or more adsorbents were likewise laid in a recess provided for this in the blister (when using 2 adsorbent packs, the 2nd adsorbent pack was loosely laid on this). The blister filled in this way was subsequently packed into a prefabricated laminated aluminium foil pouch and sealed under slight vacuum. On account of the vacuum, the pouch forms virtually a closure of the blister, so that the wound dressing was unable to fall out. In the case of the packagings mentioned, the following variations were moreover carried out:
  packaging of the bioabsorbable wound dressing prepared according to Example 1 without an adsorbent
  packaging of the bioabsorbable wound dressing prepared according to Example 1 with 1 pack of 2.0 g of silica gel
  packaging of the bioabsorbable wound dressing prepared according to Example 1 with 1 pack of 2.0 g of zeolite 4A
  packaging of the bioabsorbable wound dressing prepared according to Example 1 with 1 pack of 2.0 g of zeolite 13X
  packaging of the bioabsorbable wound dressing prepared according to Example 1 with 1 pack of 2.0 g of Silicalite-1
  packaging of the bioabsorbable wound dressing prepared according to Example 1 with 1 pack of 2.0 g of Silicalite-1 and 2.0 g of zeolite 4A
Adsorbent materials can be obtained, for example, from Multisorb.

Example 3

Degradation Behavior of the Bioabsorbable Wound Dressing

For this test, a section (about 20-30 mg) of the bioabsorbable wound dressing, which was stored in a packaging according to Example 2 for 22 days, was weighed in and added to a metallic screen insert. This is then added to a container, in which 500 ml of 0.05 M tris pH 7.4 buffer solution (Fluka 93371) are present thermostatted at 37° C. For improvement of the material exchange, the perforated basket rotates at a speed of 50 rpm. During the whole measuring period, the buffer solution is temperature-controlled at 37° C. A certain but slight mixing of the container contents takes place here. The degradation course is monitored by means of Si analysis of the liquid phase. Samples (about 1 ml of solution) are taken here at time intervals in the course of a time period of 24 hours and analysed by ICP-OES for the Si content. The result values in µg/ml are converted by the factor 1.070 to mg absolute (60.09/28.09×500/1000). The measurement values in mg absolute are plotted graphically against the measurement time points. A linear regression is carried out only by means of the linear range of the increase. The slope corresponds to the degradation in mg/h. Taking into consideration the initial weight, the relative degradation is calculated in per cent/h ([mg/h]/[mg]×100=[%/h]). For the recovery [%], the mg absolute value is multiplied by the theoretical Si content (0.38). Table 1 shows the results of the degradation test for various packagings from Example 2.

TABLE 1

Result of the degradation test

| Packaging | Storage time until the test | Rate [%/h]) | Recovery [%]) | Observation |
| --- | --- | --- | --- | --- |
| without adsorbent | 22 days | 2.8 | 67.2 | slight residue |
| Silica gel | 28 days | 10.2 | 91.7 | completely dissolved, no residues |
| Zeolite 4A | 22 days | 3.3 | 76.8 | completely dissolved, no residues |
| Zeolite 13X | 22 days | 2 | 47.3 | only partially dissolved |

TABLE 1-continued

Result of the degradation test

| Packaging | Storage time until the test | Rate [%/h]) | Recovery [%]) | Observation |
|---|---|---|---|---|
| Silicalite-1 | 28 days | 7.4 | 90.4 | completely dissolved, no residues |
| Silicalite-1 + Zeolite 4A | 28 days | 9.1 | 91.8 | completely dissolved, no residues |

Bioabsorbable wound dressings that were stored in a packaging without adsorbent degrade markedly more slowly than those that were stored in a packaging containing silica gel, Zeolite 4A or Silicalite-1+Zeolite 4A. Delayed absorbability or incomplete absorbability can lead in vivo to the situation where residues remain in the tissue, which over the longer term can cause undesired inflammatory reactions or can lead to non-physiological wound healing.

The gas phase concentrations of water and ethanol in the packagings of Example 2 after 3, 11 and 25 days were determined. In the case of the packaging without adsorbent, the concentration of water was higher by a factor of between 1.8 (3 days, Silicalite-1) and 6 (11 days, silica gel) than in the packagings with one or more adsorbents.

In the case of the packaging without adsorbent, the concentration of ethanol was even higher by a factor of over 1000 than in the case of the packaging with Silicalite-1+Zeolite 4A after 25 days.

The adsorbents thus lead to a reduction of the concentration of water and/or ethanol in the gas phase in the packaging.

The water contents of the carrier materials from the packagings of Example 2 were measured by means of NIR spectroscopy (analysis of the absorption band at 5250 $cm^{-1}$) after storage for 25 days in the packaging.

The water content of a carrier material, stored in a packaging containing Silicalite-1 as an adsorbent was on average 4.5% by weight, the water content of a carrier material stored in a packaging containing silica gel as an adsorbent was on average 3.2% by weight, and the water content of a carrier material stored in a packaging containing Silicalite-1+Zeolite 4A as adsorbents was on average 1.1% by weight.

The ethoxy contents of the carrier materials of Examples 2 after storage in the packaging of 1 day, of 8 days and of 22 days were measured.

A decrease in the ethoxy content was seen in the case of all carrier materials over a period of time—with the exception of the carrier materials that were stored together with Silicalite-1+Zeolite 4A as adsorbents. In the case of the last-mentioned carrier materials, no temporal change was to be observed within the accuracy of measurement even after 25 days. The carrier materials that were stored in a packaging containing a water adsorbent (zeolite 4A) and an ethanol adsorbent (Silicalite-1) still show biodegradability after many months.

The invention claimed is:

1. A product comprising
  a) a packaging of:
    1) a mechanically stable base element having a first cavity open towards at least one side, for removal of at least one bioabsorbable carrier material which is arranged in the first cavity,
    2) at least one adsorbent,
    3) at least one sealing foil that closes at least an opening of the first cavity,
  b) the at least one bioabsorbable carrier material, which is situated in said first cavity,
  wherein the mechanically stable base element of the packaging comprises a second cavity for receiving the at least one adsorbent,
  wherein the at least one sealing foil also closes an opening of the second cavity containing the at least one adsorbent embedded therein,
  wherein the second cavity is open on at least one side of the mechanically stable base element and the at least one sealing foil closes the openings of the first and second cavities of the mechanically stable base element which are open towards at least one side with formation of cavities and the at least one sealing foil can be peeled off by a user only for removal of the at least one bioabsorbable carrier material arranged in the first cavity,
  wherein the at least one sealing foil is applied in a perforated manner on a bridge which is present between the first and second cavities,
  wherein the at least one bioabsorbable carrier material is suitable for tissue regeneration and is selected from the group consisting of silica gel fibers and silica gel webs,
  wherein the at least one adsorbent comprises at least one member of a group consisting of an adsorbent for water and an adsorbent for ethanol,
  wherein the at least one bioabsorbable carrier material for tissue regeneration is a wound dressing, and
  wherein the first cavity has arranged therein, a floor plate, at least one channel for receiving wetting fluid and at least one bridge for the drainage of the wetting fluid.

2. The product as claimed in claim 1, wherein the first cavity is designed in height, breadth and length so that slipping of the wound dressing in the first cavity in one of three dimensions is essentially made impossible.

3. The product as claimed in claim 1, which comprises a pouch of aluminium foil or laminated aluminium foil, which completely surrounds and closes the mechanically stable base element with said at least one sealing foil.

4. The product as claimed in claim 3, wherein layer thickness of the pouch of aluminium foil or laminated aluminium foil of the packaging is at least 16 µm.

5. The product as claimed in claim 1, wherein the second cavity for receiving the at least one adsorbent forms a closed-off void formed by the mechanically stable base element itself.

6. The product as claimed in claim 1, wherein the mechanically stable base element additionally comprises a metal foil of aluminium foil or laminated aluminium foil.

7. A process for production of the product as claimed in claim 1 in which
  a) in the packaging comprising the mechanically stable base element with the first cavity open towards at least one side, the at least one bioabsorbable carrier material is inserted into the first cavity,
  b) by the sealing foil at least the first cavity, which contains the at least one bioabsorbable carrier material embedded therein, is closed such that either a heat-sealed bond completely surrounding the first cavity results between the sealing foil and a part of the mechanically stable base element or a heat-sealed bond results between parts of the sealing foil itself, so that the mechanically stable base element and the at least one bioabsorbable carrier material are situated in the sealing foil after closure,
  c) the at least one adsorbent is added to the packaging before the sealing in step b).

8. A packaging comprising:
a) a mechanically stable base element with a first cavity open towards at least one side, for removal of at least one bioabsorbable carrier material in the first cavity,
b) at least one adsorbent,
c) at least one sealing foil, that closes at least an opening of the first cavity, which contains the at least one bioabsorbable carrier material embedded therein,
wherein the mechanically stable base element of the packaging comprises a second cavity for receiving the at least one adsorbent,
wherein the at least one sealing foil also closes an opening of the second cavity containing at least one adsorbent embedded therein,
wherein the second cavity is open on at least one side of the mechanically stable base element and the at least one sealing foil closes the openings of the first and second cavities of the mechanically stable base element which are open towards at least one side with formation of cavities and the at least one sealing foil can be peeled off by a user only for removal of the at least one bioabsorbable carrier material arranged in the first cavity,
wherein the at least one sealing foil is applied in a perforated manner on a bridge which is present between the first and second cavities,
wherein the at least one bioabsorbable carrier material is suitable for tissue regeneration and is selected from the group consisting of silica gel fibers and silica gel webs,
wherein the at least one adsorbent comprises at least one member of a group consisting of an adsorbent for water and an adsorbent for ethanol,
wherein the at least one bioabsorbable carrier material for tissue regeneration is a wound dressing,
wherein the first cavity has arranged therein, a floor plate, at least one channel for receiving wetting fluid and at least one bridge for the drainage of the wetting fluid, and
wherein the packaging is suitable for packaging and/or storing of bioabsorbable carrier materials.

* * * * *